United States Patent [19]

Winchel

[11] Plant 4,620

[45] Jan. 13, 1981

[54] ROSE PLANT

[75] Inventor: Joseph F. Winchel, Harbor City, Calif.

[73] Assignee: John C. Walter, Grand Saline, Tex.

[21] Appl. No.: 32,365

[22] Filed: Apr. 23, 1979

[51] Int. Cl.[3] ..... A01H 5/00

[52] U.S. Cl. ..... Plt./11

[58] Field of Search ..... Plt./11

*Primary Examiner*—Robert E. Bagwill
*Assistant Examiner*—James R. Feyrer
*Attorney, Agent, or Firm*—Pearne, Gordon, Sessions, McCoy & Granger

[57] ABSTRACT

A new and distinct variety of hybrid tea rose produced by me crossing First Prize (U.S. Plant Pat. No. 2,774) with Piccadilly (not patented in the United States, but grown widely in Europe).

7 Drawing Figures

The present invention relates to a new and distinct variety of rose plant of the hybrid tea class which was originated by crossing First Prize (U.S. Plant Pat. No. 2,774) with Piccadilly (not patented in the United States, but hybridized by Samuel McGredy in Ireland and grown widely in Europe). The new and distinct variety was asexually reproduced by budding in Warren, Mich., the seedling was taken to Shreveport, La. 71105, where it was further asexually reproduced by budding and observed.

This rose differs from its seed parent First Prize by having a bush that produces more basal canes with smaller foliage and more thorns, with blooms that usually come one to a stem, have a shorter bud, more petals, and are a different color.

This rose differs from its pollen parent Piccadilly by having a plant with matte rather than glossy foliage and more thorns, with blooms that have more and thicker petals to give better form and substance, and are a different color.

The accompanying drawing shows typical specimens of the growth and habit of my new variety in different stages of development in October 1978 in Shreveport, La., the color as nearly true as it is possible to make the same in a color illustration of this character. The colors in the following description are taken from the color chart of the Royal Horticultural Society, where a color designation number is shown. The other color designations are ordinary dictionary terms, where no color number is assigned.

The following is a detailed description of my new rose variety:

Type: Upright bush, seedling, for garden decoration.
Class: Hybrid tea.

THE FLOWER

Locality where grown: Warren, Mich.; Shreveport, La.; Wills Point, Tex.; and Harbor City, Calif.
Flowers borne: Singly.
Continuity: Continuous throughout growing season.
Fragrance: Very slight (fruity to spicy).
Bud:
- *Size.*—Medium.
- *Form.*—High centered.
- *Color.*—Yellow (13B), with light red hues (45B) when sepals first divide.

- *Sepals.*—A few side whiskers, attractive, medium length.
- *Peduncle.*—Medium length, tiny thorns (prickles), strong and erect, reddish-green in color.

Bloom:
- *Size when fully opened.* —4 to 4½ inches average.
- *Form.*—High-centered at first, becoming more flattened, with petals remaining loosely rolled outwardly.
- *Petalage.*—30 to 35 petals, regularly arranged.
- *Color.*—Outer petals: red border (slightly darker than 54A); Base and majority of petals: yellow (11B); reverse of petals: yellow (11C); inner petals at center of flower: yellow (11B); general tone from a distance: red (red and yellow blend).
- *Color change.*—Hot sun causes more red on border of petals as bloom ages, with a red border (54B) and yellow-orange center (18B) and after three or more days, red varies on amount of sunshine, with more sunshine producing a darker red.

Petals:
- *Texture.*—Thick.
- *Appearance.*—Inside, velvety; outside, satiny.
- *Form.*—Ovoid.
- *Arrangement.*—Regularly arranged.
- *Petaloids in center.*—Few.
- *Persistence.*—Drop off cleanly.
- *Lasting quality.*—Very long on the plant, very long as a cut flower.

REPRODUCTIVE ORGANS

Stamens, filaments, and anthers:
- *Arrangement.*—Regularly arranged around styles.
- *Color.*—Yellow.

Pollen: Yellow.
Styles: Uneven length.
Stigmas: Yellow.
Hips:
- *Shape.*—Globular.
- *Size.*—Medium.
- *Color.*—Green to light orange.
- *Protrusion.*—Seeds seldom protrude.

PLANT

Growth: Vigorous with many basal breaks; bush 4 to 5 ft. high.
Foliage: Compound, mostly 5 leaflets, some 3 and 7.
- *Size.*—Medium.

*Quantity.*—Abundant.

*Color.*—New foliage: upper side slight greenish-red, underside a little more red.

Old foliage: Upper side green, underside green.

*Shape.*—Ovate with acute apex, serrated.

*Texture.*—Upper side: leathery gloss. Underside: matte.

*Edge.*—Serrated.

*Serration.*—Medium.

*Leaf stem.*—Color: greenish-red. Underside: green.

*Stipules.*—Medium length.

*Resistance to disease.*—Black spot: yes. Mildew: yes. Rust: Never experienced it.

Wood:

*New wood.*—Color: reddish-green. Bark: Smooth.

*Old wood.*—Color: green. Bark: smooth.

Thorns:

*Thorns.*—Quantity: many on main stalks. On laterals from stock: Many. Form: Curves slightly downwardly. Length: All sizes. Color: Greenish-red when young. Position: Regular.

*Prickles.*—Quantity: Profuse on main stalks. On laterals: Profuse.

Winter hardiness: Winter hardy if protected.

I claim:

1. A new and distinct variety of rose plant of the hybrid tea class, substantially as herein shown and described, characterized by the combination of a plant with many basal canes, matte foliage, many thorns, usually one bloom per stem, large, high-centered blooms of striking yellow color, with sun exposure producing an attractive red coloration at petal edges, and of good keeping qualities both on the bush and as a cut flower.

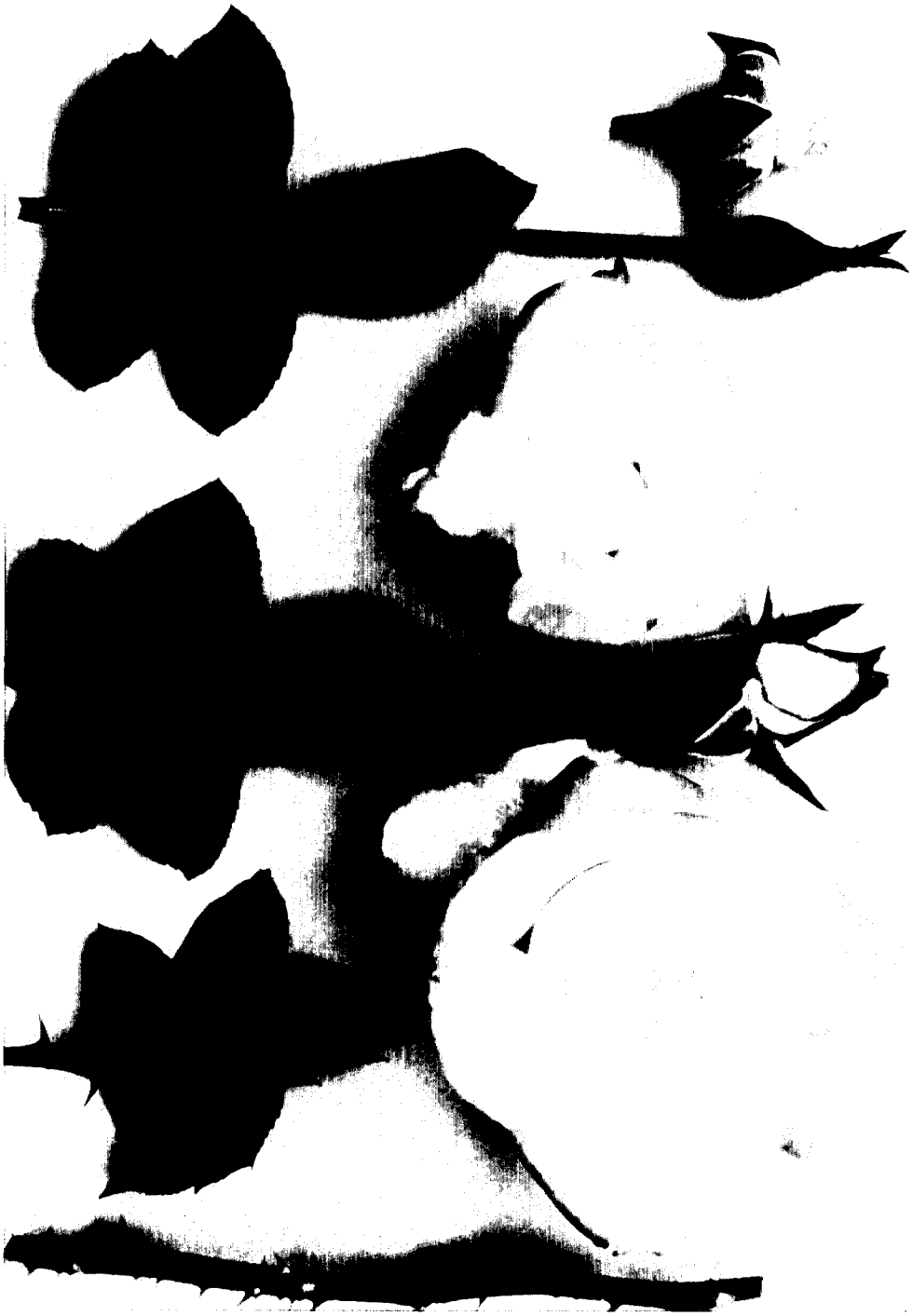

* * * * *